United States Patent [19]

Leder

[11] Patent Number: 4,542,096

[45] Date of Patent: Sep. 17, 1985

[54] DETECTING REARRANGED HUMAN C-MYC DNA FRAGMENTS ASSOCIATED WITH ONCOGENES

[75] Inventor: Philip Leder, Brookline, Mass.

[73] Assignee: President and Fellows of Harvard College, Cambridge, Mass.

[21] Appl. No.: 469,797

[22] Filed: Feb. 25, 1983

[51] Int. Cl.[4] .................... G01N 33/50; G01N 33/58
[52] U.S. Cl. ........................................ 435/6; 436/504; 935/78
[58] Field of Search ............... 435/6; 436/504; 935/78

[56] References Cited

U.S. PATENT DOCUMENTS 4,358,535  11/1982  Falkow .................................. 435/6

OTHER PUBLICATIONS

Chemical Abstracts, 98:47897m (1983).
Chemical Abstracts, 98:155778g (1983).
Chemical Abstracts, 100:115723p (1984).
C. M. Croce et al., Scientific American, 252 (3), 54–60 (Mar. 1985).
Chemical Abstracts, 97:196662n (1982).
Science, vol. 218, 983–985 (1982).
Adams et al., Proc. Natl. Acad. Sci. USA, vol. 79, 6966–6970 (1982).
Klein, Nature, vol. 294, 313–318 (1981).
Rowley, Science, vol. 216, 749–751 (1982).
Boston Globe, Oct. 13, 1982.
New York Times, Oct. 21, 1982.
Kirsch et al., Nature, vol. 293, 585–587 (1981).
Harris et al., Proc. Natl. Acad. Sci. U.S.A. vol. 79, 4175–4179 (1982).
Manolov et al., Nature, vol. 237, 33–34 (1972).

*Primary Examiner*—Sidney Marantz

[57] ABSTRACT

Rearranged DNA fragments associated with oncogenes are detected by DNA hybridization to a labelled probe comprising DNA fragment subject to rearrangement.

3 Claims, No Drawings

DETECTING REARRANGED HUMAN C-MYC DNA FRAGMENTS ASSOCIATED WITH ONCOGENES

This invention relates to detection of rearranged DNA fragments associated with oncogenes and pertains more specifically to probes for use in such detection. Detection of such rearrangement enables identification of malignant cells; the invention also is useful to detect constitutively rearranged oncogenes that predispose toward development of malignancy in affected individuals.

It has been reported that in mammalian cancers such as Burkitt's lymphoma and chronic myelogenous leukemia many malignant cells are characterized by the presence of a rearranged or translocated chromosome, a portion of which (in the case of Burkitt's lymphoma a translocated oncogene known as the myc gene) has moved from its normal chromosomal location into the region coding for the heavier of the two protein chains of antibody molecules. Science, Vol. 218, 983–985 (1982); Adams et al., Proc. Natl. Acad. Sci. USA, Vol. 79, 6966–6970 (1982).

Certain chromosomal translocations are so characteristic of specific human and murine leukemias and lymphomas that their occurrence is thought to be critical to the malignant transformation of these cells as pointed out by Klein, Nature Vol. 294, 313–318 (1981) and Rowley, Science Vol. 216, 749–751 (1982). In human Burkitt's lymphoma and murine plasmacytoma cells, these translocations have been stated to involve chromosomes upon which the immunoglobulin (Ig) genes are located. In fact, in man, these translocations involve precisely those chromosomal segments that encode the immunoglobulin genes (i.e., in Burkitt's lymphoma, reciprocal translations involve 8q24 and 14q32 (IgH), 2p13 (k) or 22q11 ($\lambda$)).

Human c-myc gene, an analogue of the avian MC-29 viral transforming gene, is located at band q24 on chromosome 8, the breakpoint for the characteristic Burkitt's translocations, and a DNA fragment containing or associated with c-myc is frequently rearranged in Burkitt's cell lines. While not all Burkitt's lymphoma cells display rearrangement, those which do exhibit such rearrangement are in fact malignant.

The invention comprises the method of identifying malignant cells in a biological sample which comprises immobilizing DNA from sample cells and from normal control cells on solid supports and subjecting said immobilized DNA to hybridization with a labelled DNA fragment subject to chromosomal rearrangement in malignant cells to determine whether rearrangement is present in said sample cells.

DNA fragment subject to rearrangement, the human m-myc fragment, was derived from a random human embryonic liver library screened with the avian v-myc gene (2.8 Kb Bam H1 fragment), and cloned. A 1.5 Kb Sst 1 fragment was subcloned and was shown by appropriate restriction enzyme digestion, blot hybridization and heteroduplex mapping to be free of Alu sequences and to represent the 5' portion of the c-myc gene as determined by probe homology to the 5' portion of the MC29 v-myc gene. This subclone was digested with Sst 1, separating the 1.5 Kb insert from plasmid sequences; the 1.5 Kb fragment was labelled with $^{32}$P by conventional procedures and used as a hybridizing probe. Plasmid containing the 1.5 Kb fragment has been deposited with the American Type Culture Collection and is identified as ATCC No. 39286 dated Jan. 31, 1983.

In using the probe to detect malignant cells, a sample of the cells to be examined, for example a biopsy specimen or a specimen of blood, etc. is lysed, DNA is extracted, digested with restriction endonucleases, subjected to electrophoresis in agarose to separate the fragments, and the cell DNA fragments are immobilized on a solid support by conventional procedures. The immobilized DNA sample is then subjected to hybridization assay with the labelled DNA fragment probe. Those samples displaying hybridization not only in the same location as the control but in an additional rearranged or translocated position as well are malignant.

EXAMPLE

Twelve different strains of human Burkitt's lymphoma cell lines, as described by Lenoir et al., Nature Vol. 298, 474–6 (1982) were obtained from the International Agency for Research on Cancer, Lyons, France and the genomic DNA from each strain prepared as described by Hieter et al., Nature Vol. 294, 536–540 (1981). The cell lines employed and the chromosome translocation in each line were as follows. BL22 (8; 14) BL31 (8; 14); Raji (8; 14); Seraphina (8; 14); BL42 (8; 14); Ly65 (8q$^-$); BJAB (none); JBL2 (8; 2); Ly66 (8; 2); BL2 (8; 22). Normal human white blood cells were used as a control.

Each DNA specimen was digested with restriction endonuclease Eco R1 and electrophoresed in 0.8% agarose gel to separate the fragments; the separated fragments were then denatured with aqueous alkali, transferred from strips of the gel to nitrocellulose filter paper, and baked in vacuum to immobilize them on the filter strips as described by Southern, J.Molec.Biol., Vol. 98, 503–517 (1975). Each specimen was then subjected to hybridization with a solution of the labelled probe containing 40% formamide and 5x SSC (SSC is aqueous 0.15M sodium chloride, 0.15M sodium citrate) for 8 hours at 47° C., washed in 0.1 SSC containing 0.1% SDS (sodium dodecyl sulfate) to remove any of the probe not specifically bound or hybridized, and subjected to radioautography.

All specimens including the normal human control exhibited hybridization of the probe to a 12.5 Kb Eco R1 fragment of DNA which corresponded to the non-rearranged allelic copy of c-myc. In addition, the probe detected separate bands representing rearrangements of the other allelic copy of this gene in BL22, BL31, Raji, Ly65 and JBL2. Other DNA specimens from the same cell lines were treated in the same way except that restriction endonuclease Bam H1 replaced Eco R1; this procedure confirmed the rearrangements of Raji, BL22 and Ly65, and in addition showed rearrangements in Seraphina and BL42.

Similar results can be obtained in the case of other malignant cells such as those of chronic myelogenous leukemia provided an oncogene has been rearranged by translocation of a DNA fragment.

What is claimed is:

1. The method of detecting rearranged human c-myc DNA fragments associated with oncogenes in a biological sample which comprises
   immobilizing DNA from sample cells and from normal control cells on solid supports
   subjecting said immobilized DNA to hybridization with a labelled fragment of human c-myc DNA subject to chromosomal rearrangement in malignant cells to determine whether rearrangement is present in said sample cells.

2. The method as claimed in claim 1 in which said cells are of human origin.

3. The method as claimed in claim 2 in which said malignant cells are Burkitt's lymphoma cells and said DNA fragment is the 1.5 Kb fragment from plasmid ATCC No. 39286.

* * * * *